United States Patent [19]

Wilson

[11] Patent Number: 5,689,834
[45] Date of Patent: Nov. 25, 1997

[54] GOGGLES

[76] Inventor: Ken Wilson, 5384 Linda Vista, Rd. #104, San Diego, Calif. 92110

[21] Appl. No.: 772,910

[22] Filed: Dec. 24, 1996

[51] Int. Cl.$^6$ ............................................. A61F 9/02
[52] U.S. Cl. ................................. 2/436; 2/435; 2/441
[58] Field of Search ........................ 2/426, 435, 436, 2/437, 439, 441, 443, 7, 8

[56] References Cited

U.S. PATENT DOCUMENTS

| | | | |
|---|---|---|---|
| 835,828 | 11/1906 | Meyrowitz | 2/437 |
| 2,130,127 | 9/1938 | Fischer | 2/435 |
| 2,612,640 | 10/1952 | Palmes | 2/436 |
| 2,619,642 | 12/1952 | Christensen et al. | 2/436 |
| 2,619,643 | 12/1952 | Christensen et al. | 2/435 |
| 3,591,864 | 7/1971 | Allsop | 2/436 |
| 3,945,044 | 3/1976 | McGee et al. | 2/436 |
| 5,018,223 | 5/1991 | Dawnson et al. | 2/436 |
| 5,542,130 | 8/1996 | Grabos, Jr. et al. | 2/436 |

FOREIGN PATENT DOCUMENTS

| | | | |
|---|---|---|---|
| 2500176 | 8/1982 | France | 2/435 |
| 380263 | 9/1923 | Germany | 2/435 |

*Primary Examiner*—Amy B. Vanatta

[57] ABSTRACT

A pair of goggles that are worn by an active sports participant which enhances the person's ability to see and protect his eyes during active sport activities. The goggles have a double lens assembly that is removably received in the front wall frame of the goggles. One or more metal heat sinks are secured to the goggle structure to dissipate the heat within the chamber between the goggles and the face of the person wearing the goggles.

12 Claims, 3 Drawing Sheets

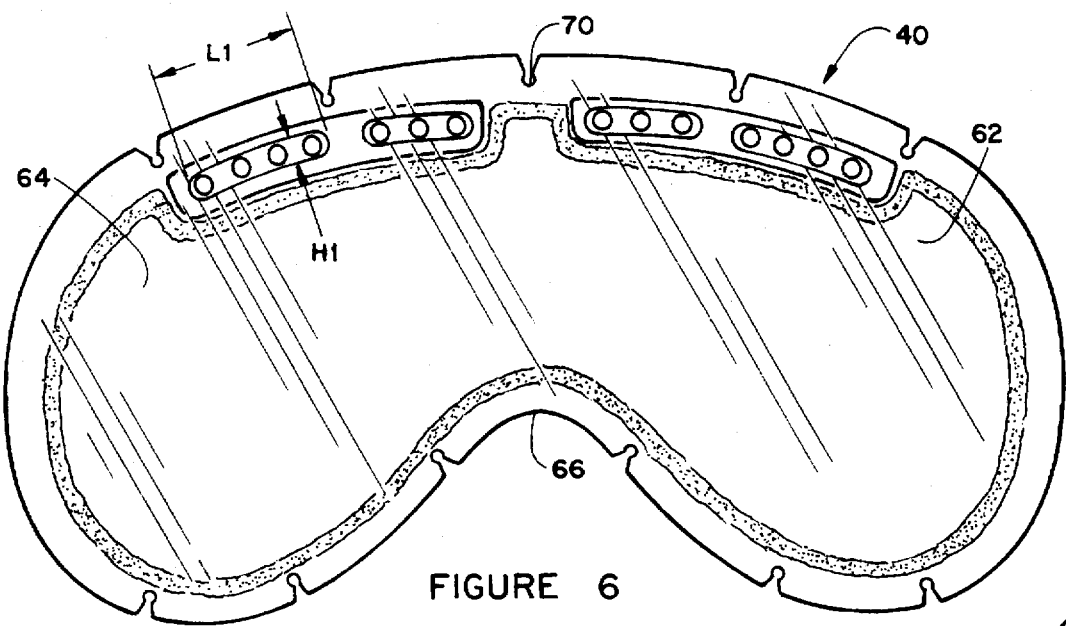
FIGURE 6
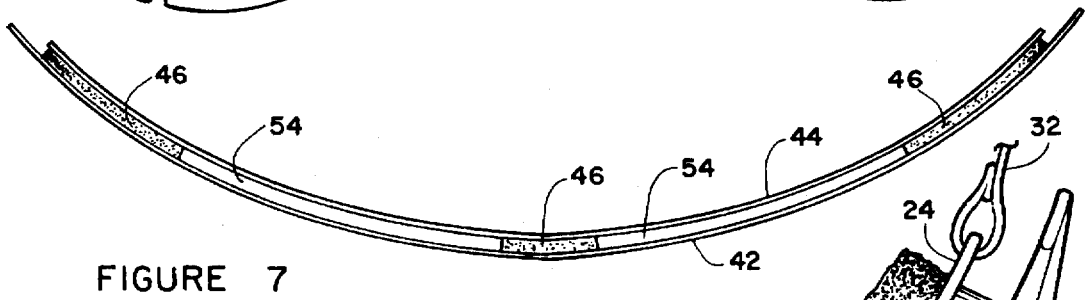
FIGURE 7
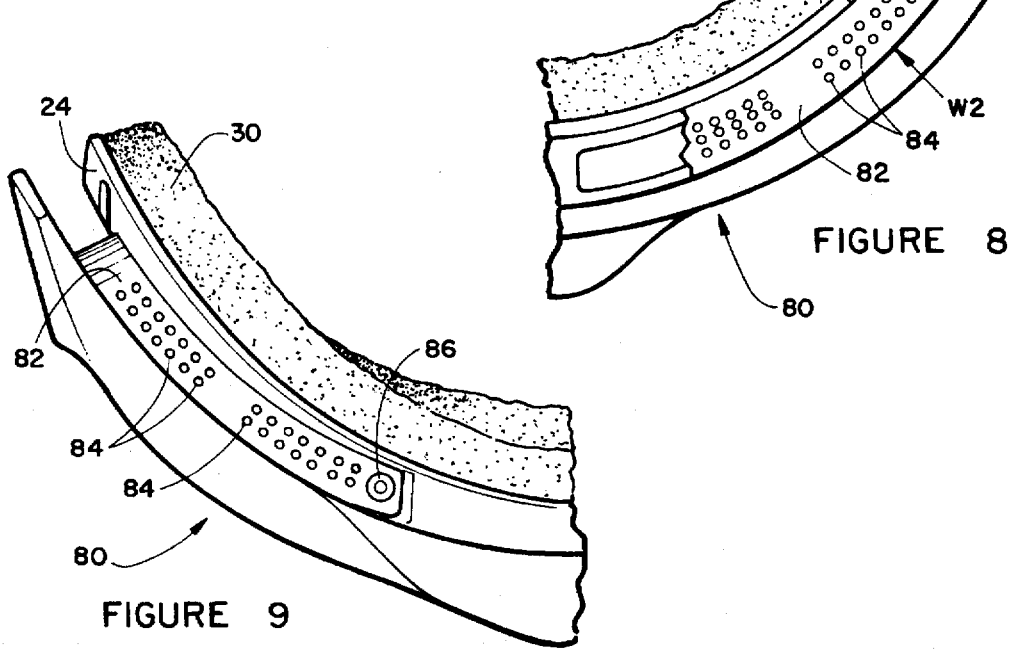
FIGURE 8
FIGURE 9

GOGGLES

BACKGROUND OF THE INVENTION

The invention relates to eyewear and more specifically to a pair of goggles that would be worn by an active sports participant.

Presently when skiing or snow boarding the goggles of a participant fog up to a degree that it is difficult or impossible to see. This is a serious problem because the sport participant can be going at speeds over 20 miles per hour. Not only does this present a danger to other people on the slopes but it can result in the sport participant running into fixed objects such as trees.

The structure of goggles used in active sports have been designed to prevent objects or particles from getting into the wearer's eyes. Accordingly, a chamber is formed between the front surface of the person's face and the inner surface of the goggles. This results in the excessive heat emanating from the wearer's face being trapped in this chamber. Since the weather conditions are normally cold, the lenses fog up due to failure of the goggles to dissipate the heat produced by the wearer.

Present day goggles attempt to ameliorate the over heating problem and the fogging of the goggles by directing air through the goggles and around the lens assembly. Also lens assemblies having spaced apart front and rear lens members have been utilized to prevent fogging of the lens assembly.

It is an object of the invention to provide a novel pair of goggles that has structure for dissipating heat from the person's face in the area that the goggles are worn.

It is also an object of the invention to provide a novel pair of goggles that can be easily manufactured with an unusual heat sink bar structure or heat sink strip of metal structure.

It is another object of the invention to provide a novel pair of goggles that are safer for active sports participants when normal conditions would cause the goggles to fog up.

SUMMARY OF THE INVENTION

The novel pair of goggles resemble a conventional goggle structure and they are provided with structure for dissipating unwanted heat from the face of the wearer that normally causes the lens assembly to fog. The goggles have a lens assembly having a conventional front lens and rear lens that are spaced from each other by a closed loop spacer strip. The spacer strip winds around between the lenses in a predetermined path to form heat sink bar pockets adjacent the top edge of the lens assembly. Into these pockets are positioned aluminum heat sink bars whose front surface is in contact with the front lens and whose rear surface is in contact with the rear lens. The heat radiating from the face of the person wearing the goggles is drawn to the heat sink bar helping to prevent the lenses from fogging.

The additional structure of air ventilation slots in the front lens that are aligned with air ventilation apertures in the heat sink bar and air vent apertures in the rear lens create a venturi effect that effectively draws heat quickly away from the heat sink bar and prevents fogging of the lenses.

An alternative embodiment of the goggles has a lens assembly having only a front lens with the heat sink bars secured to the rear surface of the front lens.

A novel strip of heat sink aluminum material can also be mounted over the air ventilation slots between the respective rib members of the goggles that connect the front wall frame to the rear frame member. This strip would replace the conventional air penetrable foam strips that are normally used. It is to be understood that the heat sink strip of aluminum material can either be used alone with a conventional lens assembly or it can be used in combination with the new lens assembly which has heat sink bar pockets for receiving the heat sink bars.

In addition to snow related sports, the goggles can also be used when participating in paint ball games, motorcross riding and other activities.

DESCRIPTION OF THE DRAWINGS

FIG. 6 is a front elevation view of the lens assembly;

FIG. 7 is a top plan view of the lens assembly;

FIG. 8 is a top plan view of an alternative embodiment of the goggles showing only one half of a symmetrical pair of goggles;

FIG. 9 is a bottom plan view of the alternative embodiment of the pair of goggles illustrated in FIG. 8 showing only one half of an symmetrical pair of goggles;

DESCRIPTION OF THE PREFERRED EMBODIMENT

Figure 1:
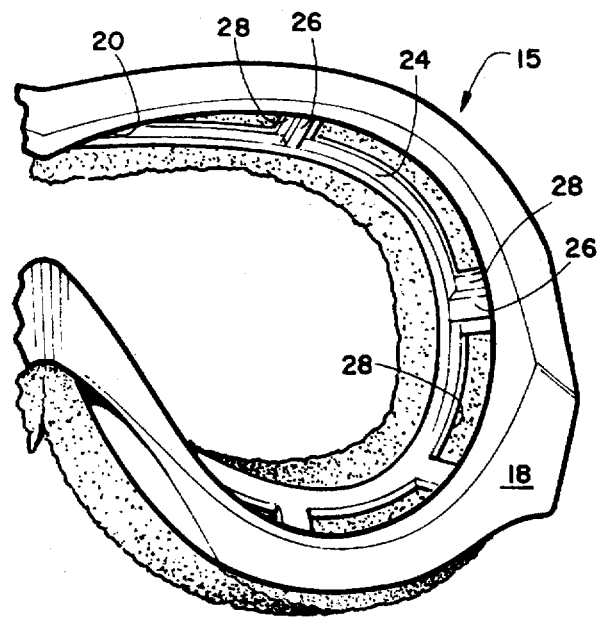
FIG. 1 is a front elevation view showing only the right half of a symmetrical pair of goggles with its lens assembly removed.
Figure 2:
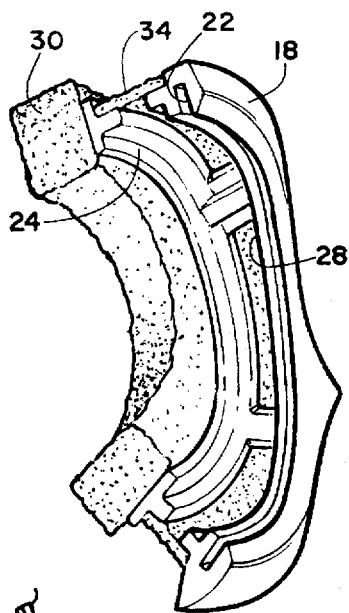
FIG. 2 is a cross sectional perspective view of the goggles structure.
Figure 3:
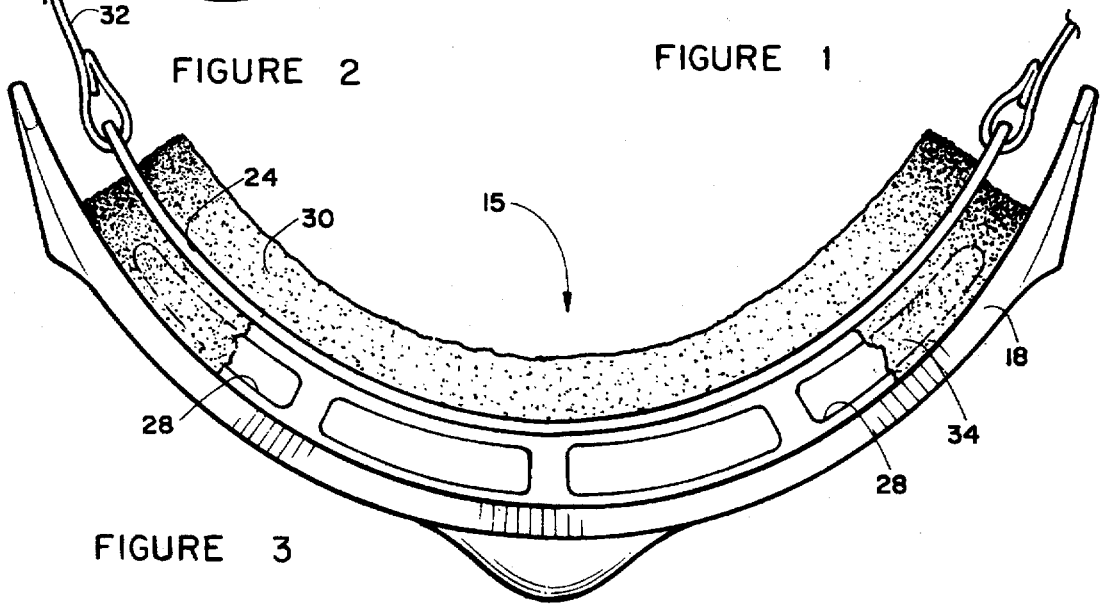
FIG. 3 is a top plan view of the pair of goggles.
Figure 5:
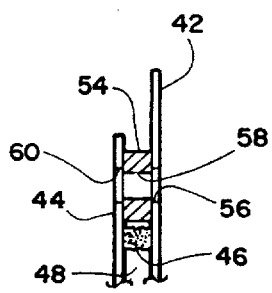
FIG. 5 is a cross sectional view taken along lines 5—5 of FIG. 4.
Figure 4:
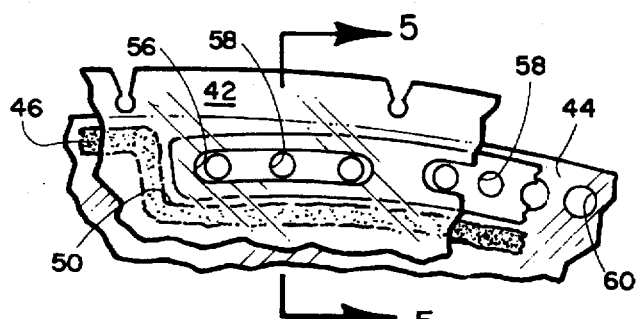
FIG. 4 is a partial front elevation view showing the top edge of the lens assembly.

The novel goggles will now be described by referring to FIGS. 1–12 of the drawings. The goggles are generally designated numeral 15.

Goggles 15 have a front wall frame 18 having a lens aperture 20 for receiving a lens assembly 40 that would cover both the wearer's left and right eyes. A lens groove 22 removably receives the peripheral edge of lens assembly 40. Goggles 15 also have a rear frame member 24. Rib members 26 have their rear ends connected to rear frame member 24 and their front ends connected to front wall frame 18. Air ventilation slots 28 are formed between the respective rib members 26.

A rear foam cushion strip 30 is secured to the rear surface of rear frame member 24 and it presses against the face of the person wearing the goggles. A headband strap 32 passes around the wearer's head to secure the goggles in position. An air penetrable strip 34, normally of foam material, covers the respective air ventilation slots 28.

Lens assembly 40 is best illustrated in FIGS. 4–7. It has a front lens 42 and a rear lens 44. They are separated from each other by a spacer strip 46 to form an air chamber 48 in the interior of the lens assembly. Spacer strip 46 is wound in a pattern that forms a pair of heat sink bar pockets 50 adjacent the top edge of the lens assembly. Each of the heat sink bar pockets 50 receives an aluminum heat sink bar 54 whose front surface contacts front lens 42 and whose rear surface contacts rear lens 44. Heat sink bar 54 may be secured to the respective surfaces of front lenses 42 and rear lens 44 by a conventional adhesive. Heat sink bars 54 have a height H1 in the range of 0.030–0.750 inches, and a thickness T1 in the range of 0.030–0.500, and a length L1 in the range of 0.300"–7". Air ventilation slots 56 are formed in front lens 42 immediately in front of heat sink bar 54. Air ventilation apertures 58 pass through heat sink bar 54 and they are aligned with air ventilation apertures 60 in rear lens 44.

Lens assembly 40 has a left eye portion 62 and a right eye portion 64. A nose recess 66 is formed along the bottom edge of lens assembly 40. A plurality of notches 70 are formed around the outer perimeter of front lens 42 and they are detachably inserted over mating structure (not shown) around the perimeter of lens groove 22.

FIGS. 8 and 9 illustrate an alternative embodiment of a pair of goggles having different heat sink structure. As illustrated, goggles 80 would be used with conventional one or two lens assemblies. A strip 82 of aluminum metal is used to cover the outer surface of air ventilation slots 28. Strip 82 has a plurality of apertures 84 to aid in ventilation of the heat which is captured by metal heat sink strip 82. Strip 82 is seen fastened by a rivet 86 but it is understood that any other conventional fastening structure could also be used. Metal strip 82 has a thickness T2 in the range of 0.010–0.250 inches, a width W2 in the range of 0.100–0.900 inches, and a length L2 in the range of 2–12 inches.

It is also to be understood that the use of the metal strip heat sink member could also be used in conjunction with the embodiment illustrated in FIGS. 1–6. In this instance air penetrable strip 34 would be replaced by aluminum metal strip 82.

Figure 10:
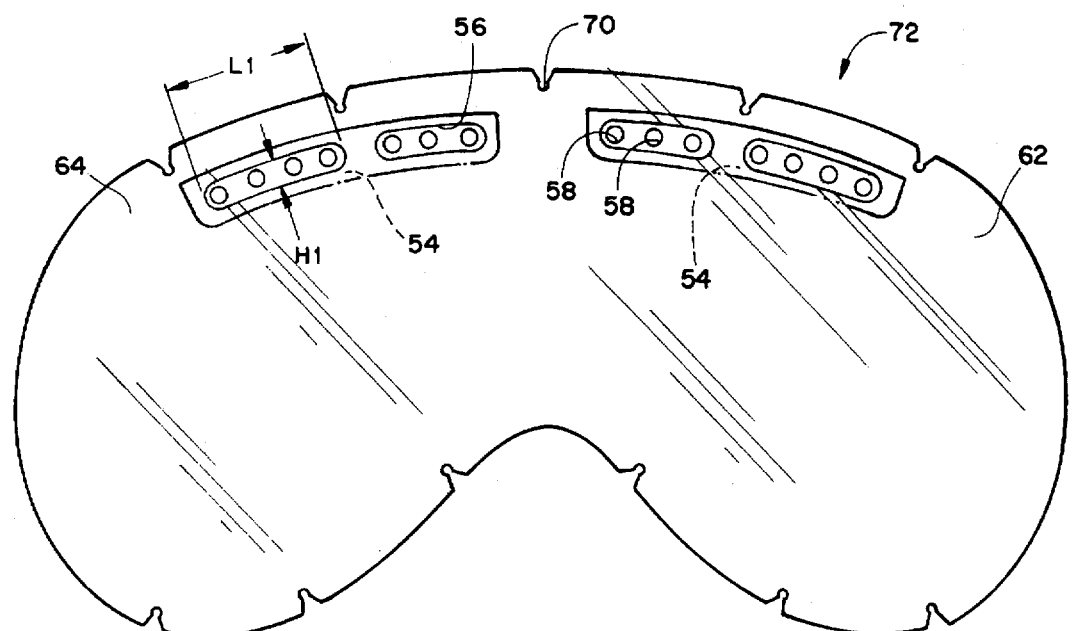
FIG. 10 is a front elevation view of an alternative embodiment of the lens assembly having only a front lens.
Figure 11:
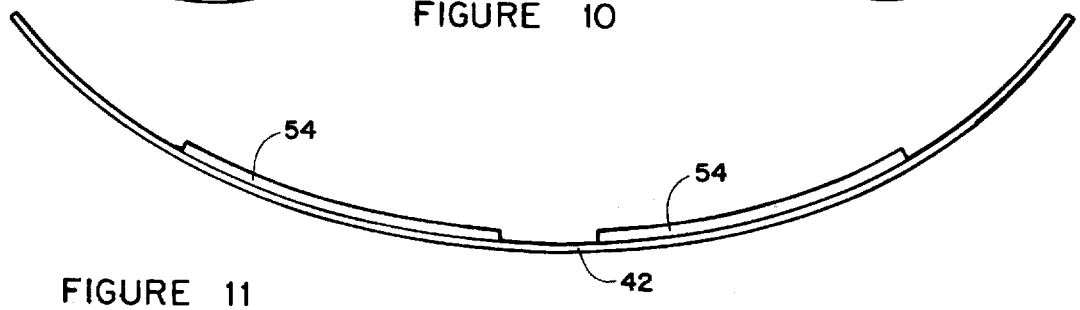
FIG. 11 is a top plan view of the lens assembly illustrated in FIG. 10.
Figure 12:
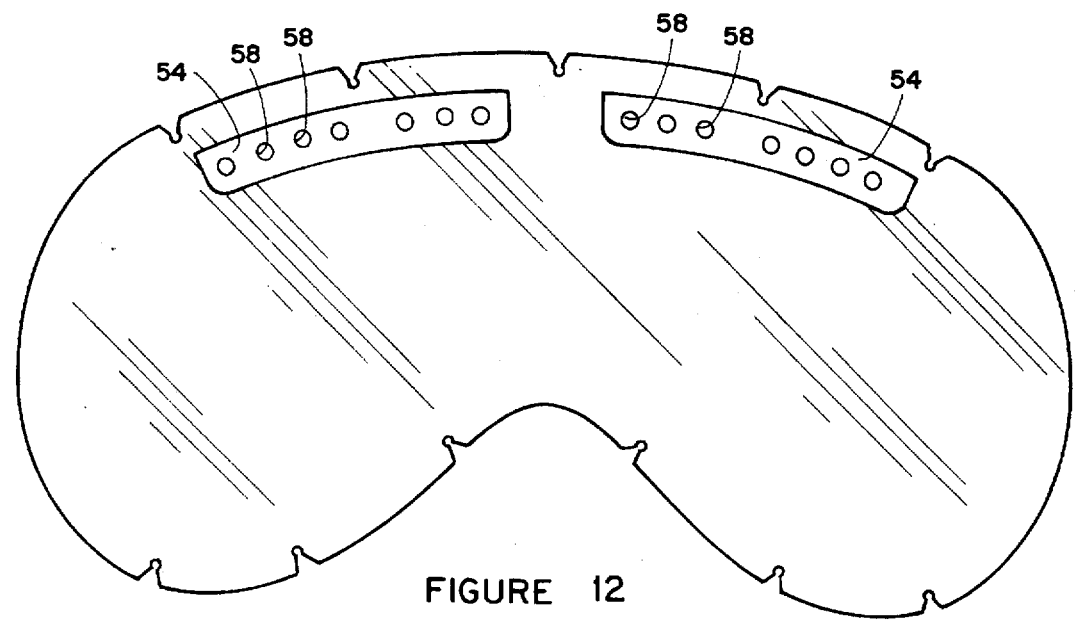
FIG. 12 is a rear elevation view of the lens assembly illustrated in FIG. 10.

An alternative lens assembly 72 is illustrated in FIGS. 10–12. The similar structure of lens assembly 72 and lens assembly 40 use the same numerical designation. Lens assembly 72 has a left eye portion 62 and a right eye portion 64. A nose recess 66 is formed along the bottom edge of lens assembly 72. A plurality of notches 70 are formed around the outer perimeter of front lens 42 and they are detachably inserted over mating structure (not shown) around the perimeter of lens groove 22. Aluminum heat sink bars 54 are secured to the rear of front lens 42 by a conventional adhesive. Air ventilation slots 56 are formed in front lens 42 immediately in front of heat sink bars 54. Air ventilation apertures 58 pass through heat sink bar 54.

What is claimed is:

1. A pair of goggles comprising:
   a front wall frame having a lens aperture for removably receiving a lens that has integrally formed left and right eye portions; said front wall frame having a rear surface;
   a rear frame member that is spaced rearwardly from said front wall frame; said rear frame member having a front surface and a rear surface;
   a plurality of rib members each having a front end and a rear end; the respective front ends of said rib members being connected to said front wall frame at spaced intervals around the rear surface of said front wall frame; the respective rear ends of said rib members being connected to said rear frame member at spaced intervals around the front surface of said rear frame member; the laterally spaced rib members define air ventilation slots between each other;
   an elongated rear foam cushion strip is secured to the rear surface of said rear frame member and it rests against a person's face when the goggles are being worn;
   a lens assembly having a front lens and a rear lens; said front lens having a rear surface and said rear lens having a front surface; means for spacing said front lens from said rear lens; said lens assembly having a top edge and a bottom edge;
   means for detachably securing said lens assembly in the lens aperture of the front wall frame of said goggles;
   at least one elongated metal heat sink bar having a front surface and a rear surface; said rear surface being in contact with the front surface of said rear lens so that it will draw heat away from said rear lens when a person wears said goggles.

2. The pair of goggles recited in claim 1 wherein said lens assembly has at least one heat sink bar pocket formed adjacent its top edge for receiving a heat sink bar between said front lens and said rear lens.

3. The pair of goggles recited in claim 1 wherein the front surface of said metal heat sink bar is in contact with the rear surface of said front lens.

4. The pair of goggles recited in claim 1 wherein there are a plurality of air ventilation apertures that pass all of the way through said front lens, said metal heat sink bar and said rear lens.

5. The pair of goggles recited in claim 1 wherein said metal heat sink bar is made of aluminum material.

6. The pair of goggles recited in claim 1 further comprising an air penetrable strip that covers the air ventilation slots between the respective rib members.

7. The pair of goggles recited in claim 6 wherein said air penetrable strip is made of metal and it functions as a heat sink and it has a plurality of air vent apertures.

8. A pair of goggles comprising:
   a front wall frame having a lens aperture for removably receiving a lens that has integrally formed left and right eye portions; said front wall frame having a rear surface;
   a rear frame member that is spaced rearwardly from said front wall frame; said rear frame member having a front surface and a rear surface;
   a plurality of rib members each having a front end and a rear end; the respective front ends of said rib members being connected to said front wall frame at spaced intervals around the rear surface of said front wall frame; the respective rear ends of said rib members being connected to said rear frame member at spaced intervals around the front surface of said rear frame member; the laterally spaced rib members define air ventilation slots between each other;
   an elongated rear foam cushion strip is secured to the rear surface of said rear frame member and it rests against a person's face when the goggles are being worn;
   a lens assembly having a front lens and a rear lens; said front lens having a rear surface and said rear lens having a front surface; means for spacing said front lens from said rear lens; said lens assembly having a top edge and a bottom edge;
   means for detachably securing said lens assembly in the lens aperture of the front wall frame of said goggles;
   an air penetrable strip that covers the air ventilation slots between the respective rib members; said air penetrable strips being made of metal and it functions as a heat sink and it has a plurality of air vent apertures.

9. The pair of goggles recited in claim 8 wherein said air penetrable strip is made of aluminum material.

10. A pair of goggles comprising:
    a front wall frame having a lens aperture for removably receiving a lens that has integrally formed left and right eye portions; said front wall frame having a rear surface;
    a rear frame member that is spaced rearwardly from said front wall frame; said rear frame member having a front surface and a rear surface;

a plurality of rib members each having a front end and a rear end; the respective front ends of said rib members being connected to said front wall frame at spaced intervals around the rear surface of said front wall frame; the respective rear ends of said rib members being connected to said rear frame member at spaced intervals around the front surface of said rear frame member; the laterally spaced rib members define air ventilation slots between each other;

an elongated rear foam cushion strip is secured to the rear surface of said rear frame member and it rests against a person's face when the goggles are being worn;

a lens assembly having a front lens having a rear surface; said lens assembly having a top edge and a bottom edge;

means for detachably securing said lens assembly in the lens aperture of the front wall frame of said goggles;

at least one elongated metal heat sink bar having a front surface and a rear surface; said front surface being in contact with the rear surface of said front lens so that it will draw heat away from said rear lens when a person wears said goggles.

11. The pair of goggles recited in claim 10 wherein there are a plurality of air ventilation apertures that pass all of the way through said front lens and said metal heat sink bar.

12. The pair of goggles recited in claim 10 wherein said metal heat sink bar is made of aluminum material.

* * * * *